United States Patent
Eck et al.

(10) Patent No.: US 7,125,166 B2
(45) Date of Patent: Oct. 24, 2006

(54) METHOD AND DEVICE FOR AUTOMATIC TESTING OF AN X-RAY SYSTEM

(75) Inventors: Kai Eck, Aachen (DE); Hans-Aloys Wischmann, Aachen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 135 days.

(21) Appl. No.: 10/503,378

(22) PCT Filed: Jan. 29, 2003

(86) PCT No.: PCT/IB03/00340

§ 371 (c)(1),
(2), (4) Date: Aug. 3, 2004

(87) PCT Pub. No.: WO03/067937

PCT Pub. Date: Aug. 14, 2003

(65) Prior Publication Data

US 2005/0226382 A1    Oct. 13, 2005

(30) Foreign Application Priority Data

Feb. 5, 2002    (DE) ................................. 102 04 543

(51) Int. Cl.
*G01D 18/00* (2006.01)
(52) U.S. Cl. ....................................... 378/207; 378/117
(58) Field of Classification Search ................ 378/117, 378/207
See application file for complete search history.

(56) References Cited

U.S. PATENT DOCUMENTS

| 4,379,481 | A | 4/1983 | Juner et al. |
| 4,398,191 | A | 8/1983 | Schoepf |
| 6,204,762 | B1* | 3/2001 | Dering et al. ............... 340/541 |
| 6,720,874 | B1* | 4/2004 | Fufido et al. ............... 340/541 |
| 7,010,082 | B1* | 3/2006 | Hein et al. .................... 378/18 |

FOREIGN PATENT DOCUMENTS

| EP | 0 874 536 | 10/1998 |
| EP | 1 164 598 | 12/2001 |

OTHER PUBLICATIONS

Berkvens, P., et al.; The ERSF beamline personnel safety system; 5th EPAC96; Inst of Phys Pub, UK, 1997, pp. 2615-2617.

* cited by examiner

*Primary Examiner*—Courtney Thomas
*Assistant Examiner*—Jurie Yun

(57) ABSTRACT

The invention relates to a method and a device for automatic testing of an X-ray system (2). The doors (5a, 5b) leading to the room (1) in which the X-ray system (2) is installed are monitored by way of sensors (4a, 4b). Furthermore, the state of the room (1) can be monitored by means of further sensors such as video cameras (3). Automatic testing of the X-ray system (2) while utilizing X-rays is started only if and for as long as all doors are closed and the other sensors do not indicate that a safe state is abandoned. The device may also include facilities for automatically positioning a phantom in the beam path. Such facilities may in that case include a phantom which is provided on a flexible foil.

13 Claims, 4 Drawing Sheets

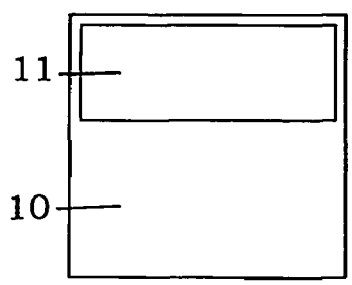
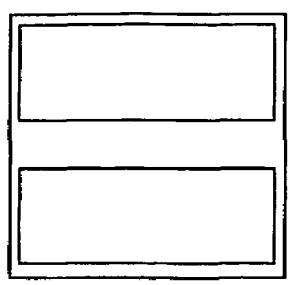
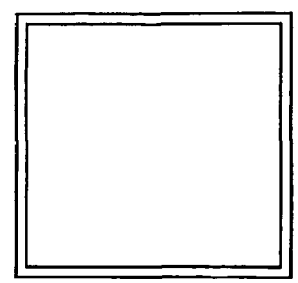
FIG.6a  FIG.6b  FIG.6c
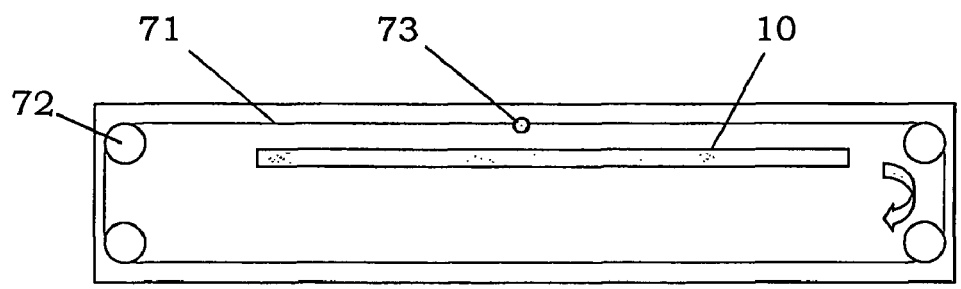
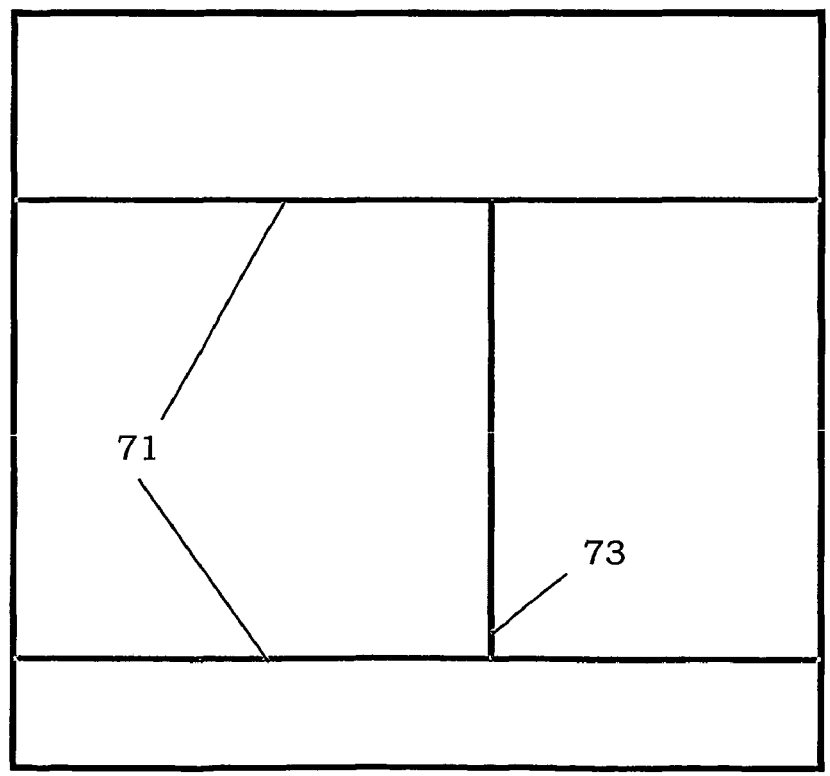
FIG.7

METHOD AND DEVICE FOR AUTOMATIC TESTING OF AN X-RAY SYSTEM

The invention realtes to a method as well as to a device for automatic testing of an imaging X-ray system while generating X-rays.

Imaging X-ray systems are widely used in the medical field as well as in other applications such as the testing of materials. They include an X-ray source for generating X-rays which irradiate an object to be examined and are subsequently detected by an X-ray detector.

The parameters of such X-ray systems which are of decisive importance in respect of the actual imaging tend to drift in the course of time. Generally speaking, such drift leads to a deteriorated performance of the imaging system. For example, when the image quality of a medical X-ray system has deteriorated beyond a given limit, the X-ray system will be tested by technicians upon request by the hospital staff. Such testing includes the acquisition of gain images and other calibration images. Because X-rays must be generated so as to acquire the images, for reasons of safety the test procedure must be monitored continuously by qualified personnel. It is to be noted in this respect that, for example, in the case of a flat dynamic X-ray detector (FDXD), a gain calibration requires approximately twenty minutes for a combination of gain and mode; during this entire period an operator must be present so as to prevent radiation accidents and to exchange test phantoms. In future generations of detectors, typically involving seven modes and four sets of gains, the calibration duration overall will even amount to several hours. During a test, however, not only time and work have to be spent by the staff directly involved, but costs are also incurred and problems arise because of the fact that the X-ray system cannot be used for its normal duties. Because of these problems, recalibration of the system is carried out only comparatively rarely nowadays, meaning that a given deterioration of the image quality has to be tolerated.

In order to accelerate and simplify the testing of the image quality of an X-ray system, EP 0 874 536 A1 proposes a specially configured phantom. A phantom is to be understood to mean an object of known shape and structure which for test purposes can be introduced into the beam path between the X-ray source and the X-ray detector in order to determine how it is imaged by the X-ray system. The phantom proposed in EP 0 874 536 A1 is arranged especially to enable measurement of given aspects of the image quality, such as the resolution and contrast, in a single X-ray image. However, it does not enable more comprehensive testing of the X-ray system.

Considering the foregoing it is an object of the present invention to provide a method, a system and a device for testing an imaging X-ray system which enable significantly simpler and more economical testing.

These objects are achieved by means of a method as disclosed in the characterizing part of claim 1, by a method as disclosed in the characterizing part of claim 5, by a device as disclosed in the characterizing part of claim 6, by a device as disclosed in the characterizing part of claim 8, by an apparatus as disclosed in claim 11 and by a system as disclosed in claim 14. Advantageous further embodiments are disclosed in the dependent claims.

In conformity with a first aspect, the invention relates to a method for the automatic testing of an imaging X-ray system while generating X-rays, the testing being understood to mean here and hereinafter a self-test, a recalibration for the compensation of parameter drifts, the start of an algorithm or a search tree for fault finding or the like. While the method is being carried out, the preservation of a defined safe state in a safety zone around the X-ray system is monitored by means of at least one sensor, and the generating of X-rays is interrupted if said safe state is abandoned.

Because of the automatic monitoring by means of the at least one sensor, the proposed method ensures that a safe state is maintained around the X-ray system while the test is being carried out, so that humans cannot be endangered by the X-rays generated. Such automatic monitoring of the safety is a prerequisite for automation of the testing of the overall X-ray system such that the continuous presence of a technician can be dispensed with.

In conformity with a preferred version, the closed state of at least one access which leads directly or indirectly to the safety zone around the X-ray system and can be opened and closed per definition forms part of the safe state. The safety zone can then be defined notably as the room in which the X-ray system is installed and the access may be formed by a door, a window or the like. Preferably, the safe state involves the closed state of all accesses leading directly or indirectly to the safety zone, for example, the closed state of all doors of the room in which the X-ray system is installed. The monitoring of the doors leading to the X-ray system ensures that no person can accidentally enter the zone around the X-ray system while the method is being carried out; otherwise such a person would be exposed to hazardous X-rays. The presence of a technician can in that case be limited to a starting phase of limited duration in which it is ensured that no person is present in the room in which the X-ray system is installed.

In conformity with a further version of the method the pattern of sensor signals determined or observed during a definition phase is used to define the safe state of the environment of the X-ray system. The method can thus be flexibly adapted to different locations of use (for example, different hospitals) in that each time different patterns of sensor signals are observed. Under the supervision by a technician, a given pattern of sensor signals can then be defined as that of the safe state, after which the subsequent monitoring of the preservation of the safe state can take place automatically.

In a further preferred version of the method the monitoring of the safe state commences when firstly all doors leading directly or indirectly to the room in which the X-ray system is installed (including other accesses for persons) have been closed (and remain closed) except for one door, and when secondly an activation signal associated with the last door commences while the last door is still open and ends when the last door is closed. For example, such a procedure allows a technician wishing to start the automatic test method to close all access doors to the room in which the X-ray system is installed, except for a last door, while making sure that there is not other person present in this room. After this condition has been satisfied, the technician can initiate, for example, by way of an actuation button provided on the outside of the last door, a signal while the last door is still open and sustain this signal until the last door has been closed. The provision of the actuation button outside the room in which the X-ray system is installed ensures that the technician has then also left the room.

In conformity with a second aspect the invention relates to a method for the automatic testing of an imaging X-ray system while generating X-rays, in which a phantom is automatically introduced into the space between the X-ray source and the X-ray detector during the test and at least one image is acquired while the phantom is present in the beam path. Preferably, in addition at least one image is acquired while the phantom is not present in the beam path. Furthermore, during an exposure the phantom can also be automatically moved in the beam path between the X-ray source and the X-ray detector, so that time effects can be investigated.

A method of this kind is carried out preferably in combination with a method of the kind described above, that is, with sensor-based monitoring of a defined safe state of the environment of the X-ray system and with automatic interruption of the X-rays when the safe state is abandoned.

The automatic introduction of the phantom in the beam path enables various calibration images to be formed without it being necessary for an operator to exchange or remove the phantom by hand. The entire testing process can thus be performed automatically, for example, during the night. Furthermore, the different positioning or the movement of the phantom in the zone between the X-ray source and the detector enables a spatially resolved examination of the image quality, because the phantom can be arranged in different positions within the imaging zone. This in turn enables a diagnosis and localization of defective components in the detector, so that fault finding can be performed prior to the dedicated deployment of service personnel. Furthermore, it is feasible that after the execution of the test method, maintenance is requested actively or automatically if such maintenance appears to be necessary on the basis of the test results.

The invention also relates to a device for automatic testing of an imaging X-ray system while generating X-rays, which device includes the following elements:
a) at least one sensor for monitoring a safety zone around the X-ray system, and
b) a control unit which is coupled to the sensor and to the X-ray system and is arranged to interrupt the generating of X-rays when the sensor signals indicate that a defined safe state is abandoned.

The invention preferably includes actuation elements whereby the testing of the X-ray system can be started and/or interrupted. The device is suitable for carrying out a method in conformity with the first aspect of the invention, so that automatic testing of the system can be achieved while safety is ensured at the same time.

The sensors for monitoring the environment of the X-ray system may notably include one or more of the following sensors:

Door contacts for detecting the closed state of accesses such as notably doors.

Motion detectors for detecting a motion taking place in the vicinity of the X-ray system, so that notably the undue presence of a person in the vicinity of the X-ray system can be detected. Such motion detectors may operate on the basis of infrared signals, ultrasound signals (for example, while utilizing the ultrasound Doppler effect) and/or video signals which can be analyzed by means of image processing software for the detection of changes in the image.

Gas detectors whereby a change of the atmosphere in the safety zone can be recognized. Such detectors may notably be carbon dioxide sensors which detect an increase of $CO_2$ due to the respiration of a person present.

Pressure sensors which are capable of detecting contact by a person present in the safety zone. Notably mats on the floor may be provided with load detectors which initiate a signal when stepped upon.

Light barriers which are capable of detecting an interruption due to a person present in the beam path. The light barriers can extend, for example, through the room in the vicinity of the X-ray system and be deflected a number of times by reflective surfaces on their way from the source to the detector. Furthermore, the safety zone can be very narrowly limited to the radiation zone (radiation cone) of the (primary) X-rays while the borders of this safety zone are monitored by a dense network of light barriers or by a light barrier surface. Transgression of these borders would then lead immediate switching off of the X-rays, so that the object invading the safety zone would no longer be exposed to danger. Preferably, the light barriers operate in a pulsed mode, for example, at a frequency of 300 Hz, in order to enable reliable discrimination between their signal and background light.

An acoustic sensor, for example, in the form of a microphone with a monitoring system connected thereto.

The X-ray detector of the X-ray system, in which case an object invading the beam path would be recognized on the basis of the resultant change of the X-ray image. To this end, for example, an image analysis system could detect any deviation from the expected image and initiate the switching-off of the X-rays in response thereto.

Finally, the invention also relates to a device for the automatic testing of an imaging X-ray system while generating X-rays, Which testing device includes a device for the automatic positioning of at least one phantom in the zone between the X-ray source and the detector. A device of this kind is suitable for carrying out the described method in conformity with the second aspect of the invention in which at least one image is acquired by means of the phantom.

In conformity with a first embodiment, the phantom may be provided on a flexible carrier, for example a foil or a wire, the carrier being transported, via guide rollers, in the zone between the X-ray source and the X-ray detector. Activation of drive rollers enables concerted movement of such a flexible carrier in a simple manner, so that the phantom can be positioned in front of the detector as desired. The flexible carrier can be transported in the form of an endless loop via a plurality of guide rollers, or be wound onto and from a roller at both its ends.

In conformity with a further embodiment, the phantom is journaled so as to be pivotable about a pivot axis, so that it can be moved to, or be positioned differently in, the beam path between the X-ray source and the X-ray detector by way of a simple pivoting motion.

The invention will be described in detail hereinafter, by way of example, with reference to the Figures. Therein:

FIG. 6 shows various feasible arrangements of the phantoms of the FIGS. 2 to 5 in a plan view;

FIG. 7 shows a side elevation and a plan view of a fifth embodiment with a phantom formed by a wire.

Figure 1:
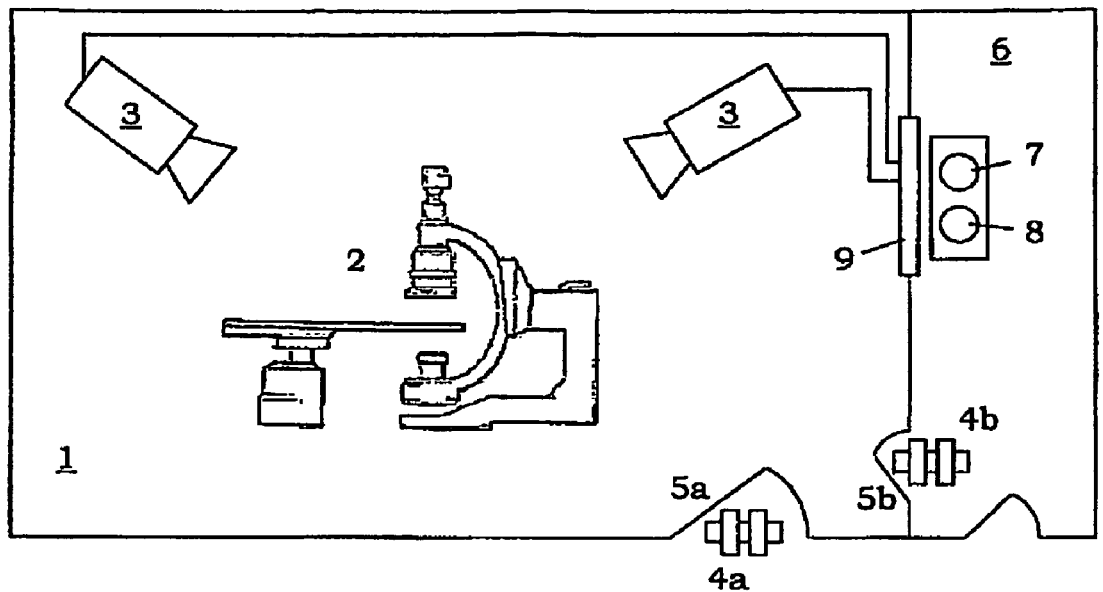
FIG. 1 is a diagrammatic representation of the vicinity of an X-ray system which is monitored by means of the method in accordance with the invention.

FIG. 1 is a diagrammatic representation of the environment of a medical imaging X-ray system 2 which may be, for example, an X-ray catheter laboratory or also a computed tomography apparatus. It is necessary to test an X-ray system of this kind from time to time; such a test may include notably a recalibration for the compensation of parameter drifts, but also a self-test or an automatic fault diagnosis. A test of this kind should be carried out without risks to the hospital staff, patients or other persons and, because the duration of the test typically amounts to several hours, it should be carried out without constant monitoring by an operator.

In order to automate a test method and to ensure the safety, the invention proposes a device which is capable of interrupting, if necessary, the test at any instant so as to change over to normal operation and which, moreover, is capable of carrying out all operations necessary for the test, notably the positioning of a phantom in the beam path. An automatic method for the testing of system components which require X-rays for calibration (for example, gain calibration) can make a substantial contribution to the reduction of the operating costs and the need for staff and at the same time ensure an imaging performance which is stable in time.

Probably the most important problem encountered in the automation of test tasks of an X-ray system while generating ionizing radiation consists in ensuring that persons cannot be unintentionally and accidentally exposed to the X-rays. Persons that could be endangered are, for example, cleaning staff, physicians preparing the examinations, technicians and/or patients on their way through the hospital or to an examination.

In this respect FIG. 1 shows, by way of example, a device in accordance with the invention for the prevention of radiation accidents. The X-ray system 2 to be tested is installed in a room 1 which can be accessed via two doors 5a and 5b. The room 1 is adjoined by a control room 6 wherefrom the X-ray system 2 can be controlled. In accordance with the invention, prior to the automatic testing of the X-ray system 2 a qualified human operator verifies that a safe state exists in a safety zone around the X-ray system 2 (that is, in the room 1). Subsequently, this safety state is "preserved" in a sense that all relevant changes of the safe state are automatically detected and automatically give rise to an immediate stop of the generating of X-rays as well as to a reset of the system to the standby state. This behavior is achieved essentially by means of three system components:

Monitoring sensors at all entrances to the room 1 in which the X-ray system 2 is installed. In the device shown in FIG. 1 these monitoring sensors are realized in the form of door contacts 4a and 4b which can detect and inform the control room 6 as to whether the doors 5a and 5b are closed or not.

A control element for starting the automatic test procedure, which element may be realized, for example, in the form of a "CALIBRATION ENABLE" button 7 in the control room 6.

A control unit 9 which is connected to suitable sensors such as the door contacts 4a, 4b and is arranged to detect a breach of the isolation of the room 1 as well as to deactivate the X-ray system 2 in response thereto. The sensors may also include, for example, one or more video cameras 3 with appropriate image analysis software enabling the detection of changes in the images of the room 1. Furthermore, infrared or Doppler ultrasound motion detectors, gas detectors, a microphone, light barriers or the like may also be connected to the control unit 9 (not shown). Moreover, the detector of the X-ray system 2 may be coupled to a (comparatively simple) image analysis device which detects the presence of unexpected structures in the X-ray image. For example, it could be detected if a hand of a person present in the room were to invade the beam path of the active X-ray system 2.

The device shown in FIG. 1 can be set to a self-test/calibration mode when all doors 5a, 5b to the room 1 are closed and the "CALIBRATION ENABLE" button 7 in the control room 6 is pressed. The test radiation is then released after visual inspection of the room 1 by an authorized physician, a technician or other person authorized to carry out X-ray examinations or calibrations.

If, as opposed to the situation shown in FIG. 1, there is no control room 6 enabling complete visual inspection of the X-ray system 2, preferably, the "CALIBRATION ENABLE" buttons 7 are provided at each entrance. In this arrangement the physician or technician must keep the button 7 depressed during the closing of the door so as to generate an activation signal. This activation signal is considered to be valid by the control unit of the system when firstly all entrances but one are closed when the button is depressed and remains closed during the entire preservation procedure, and when secondly the door neighboring the button is open when the button is depressed and closed when the button is released.

In response to said activation signal, the control unit starts to check the state of all safety points at the entrances to the room 1 in which the X-ray system 2 is installed. If the "sealing" of the room 1 is in order, the sensors present monitor the state of the room for a given period of time so as to acquire a pattern of sensor signals associated with a normal, undisturbed safe state of the X-ray room. The pattern may include measurements of a series of sensors, use preferably being made of an inexpensive video camera 3 in conjunction with standard software for image processing. After the sensor pattern of the safe state has thus been acquired and tested for consistency as well as slow changes in time, the calibration procedure is started.

The calibration procedure is terminated again when one of the following conditions is satisfied:
1. A "CALIBRATION DISABLE" button 8 arranged in the vicinity of the "CALIBRATION ENABLE" button is depressed.
2. One of the doors 5a, 5b of the sealed room 1 is opened.
3. The control unit detects, by way of the connected sensors 3, a suspicious activity in the sealed room 1, for example, on the basis of deviations from the acquired sensor pattern which are caused by a motion.

In the case of such an interruption, the device returns to a standby state in which it is ready again for image acquisition.

Preferably, at all entrances 5a, 5b there are provided alarm signals which indicate the X-ray activity so that unintentional interruption of the calibration or the self-test by a person entering the room is extremely unlikely.

In order to minimize the necessity of control interventions, the device should be capable of automatically executing as many activities as possible for a self-test. Whereas an automated gain calibration requires only an initialization of the SID (Source Image Distance) and the collimator position (if it is not yet automated), the testing of the operational behavior of the system and the entry into a search tree for fault finding require one or more phantoms in the vicinity of the detector. Hereinafter, various arrangements for automatically positioning test phantoms for testing the modulation transfer function (MTF) and the DQE (Detective Quantum Efficiency) into the beam path will be described in detail hereinafter with reference to the FIGS., 2 to 8.

Figure 2:
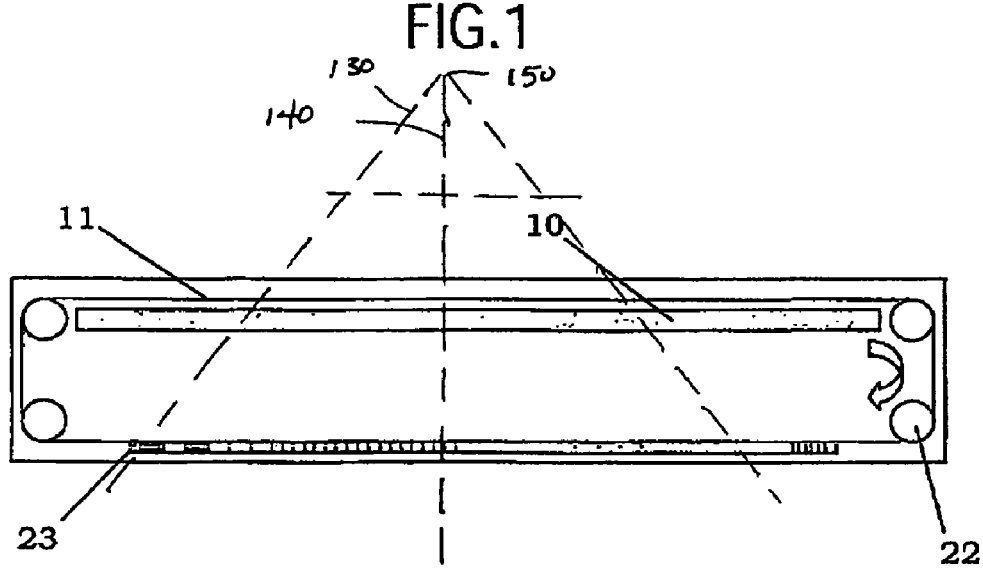
FIG. 2 shows a first embodiment of a phantom which is provided on a flexible foil, the foil being transported in the form of an endless loop.

FIG. 2 is a cross-sectional view of an X-ray detector with an X-ray-sensitive layer 10, the phantom 23 being provided on a foil 11 of a synthetic material. The synthetic foil 11 is guided in an endless loop around the sensitive layer 10 by way of four guide raflers 22; in the situation shown, the phantom 23, being made of flexible lead, is situated in the standard position underneath the detector, that is, not in the beam path. When a test is carried out, the foil 11 with the phantom 23 on the upper side can be moved in front of the sensitive layer 10 by driving at least one of the rollers 22, so that the phantom is situated in the beam path from the X-ray source to the detector. The X-ray source is an X-ray beam 130 represented by a line of dots and dashes being propagated on an axis 140. The beam emanates from a focus 150 situated in an X-ray tube not represented.

Figure 3:
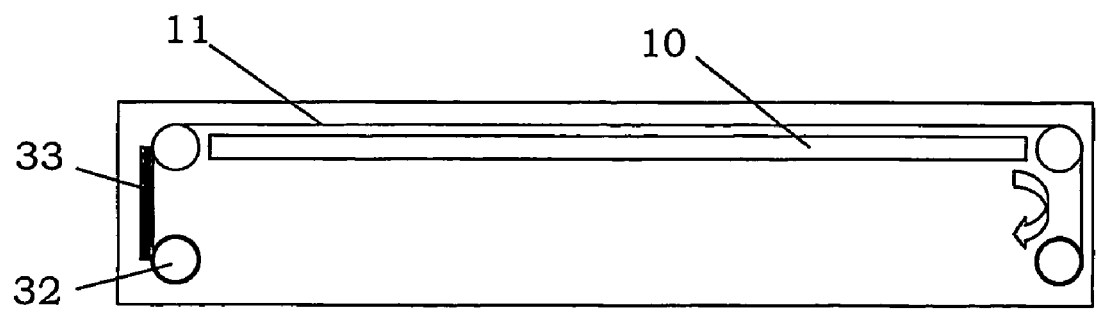
FIG. 3 shows a second embodiment of a phantom provided on a flexible foil, the foil being wound onto rollers at its ends and it being possible to move the phantom to a lateral position.

FIG. 3 is a cross-sectional view of an alternative embodiment of the described device; as opposed to FIG. 2, the carrier foil 11 is not guided in an endless loop but is wound around a respective roller 32 at both its ends. In the standard state the phantom 33 is situated to the side of the sensitive surface 10. The phantom 33 can be positioned in front of the surface of the detector by unwinding the carrier foil 11 from one roller and onto the other roller 32. The arrangement shown offers easy access to the detector from the rear thereof.

Figure 4:
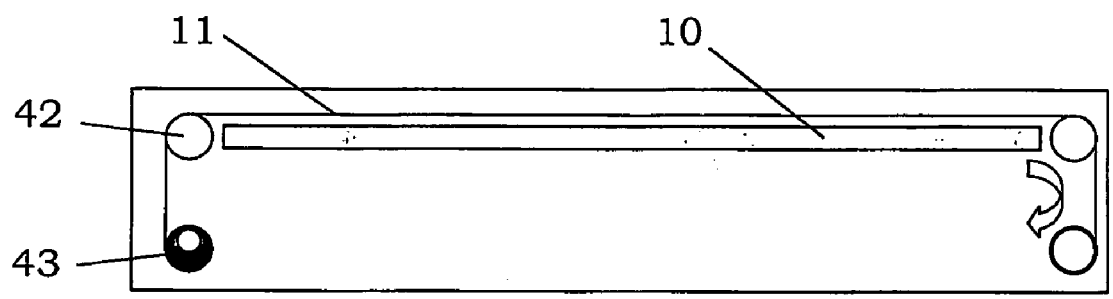
FIG. 4 shows a third embodiment of a phantom provided on a flexible foil, the foil with the phantom being wound onto rollers at its ends.

FIG. 4 shows a further embodiment of the described device in which the phantom 43 and the carrier 11 are wound together onto a roller at the side of an end when it is not to be positioned in front of the sensitive surface 10.

Figure 5:
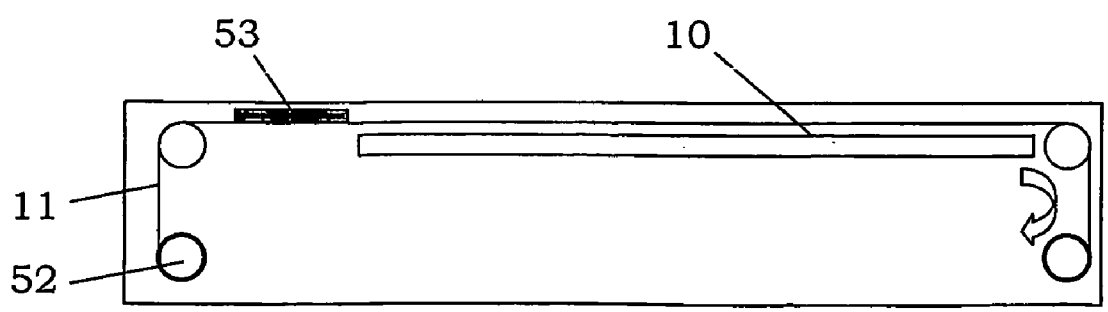
FIG. 5 shows a fourth embodiment of a phantom provided on a flexible foil, the foil being wound onto rollers at its ends and it being possible to position the phantom in a non-sensitive zone adjacent to the detector.

FIG. 5 shows a further embodiment of the device of FIG. 3 in which the phantom 53 is arranged in a zone adjacent to the sensitive surface 10 in the front plane of the detector when it is not in use. This arrangement offers the advantage that the phantom 53 need not run over a kink of the carrier foil 11 so as to be removed from the position in front of the sensor surface 10.

The foils 11 shown in the FIGS. 2 to 5 may also cover less than the entire width of the detector so as to enable easy access to the wiring and the cooling system. FIG. 6 shows, in a plan view, three examples of feasible arrangements of carrier foils 11. In the version a) approximately half the detector surface 10 is covered by a foil 11; in the version b) parts of the detector surface are covered by two foils, and in the version c) the entire detector surface is covered; the latter version necessitates lateral access to the wiring of the detector.

FIG. 7 shows an alternative embodiment of a phantom which is formed by a wire 73. The ends of the wire 73 are attached to a carrier wire 71, the carrier wire being guided, like the foil 11 in FIG. 2, around the sensitive surface 10 in an endless loop. The wire 73 can thus be positioned at option in front of the surface 10 or be removed from the beam path by rotating at least one of the rollers 72 about its longitudinal axis.

Figure 8:
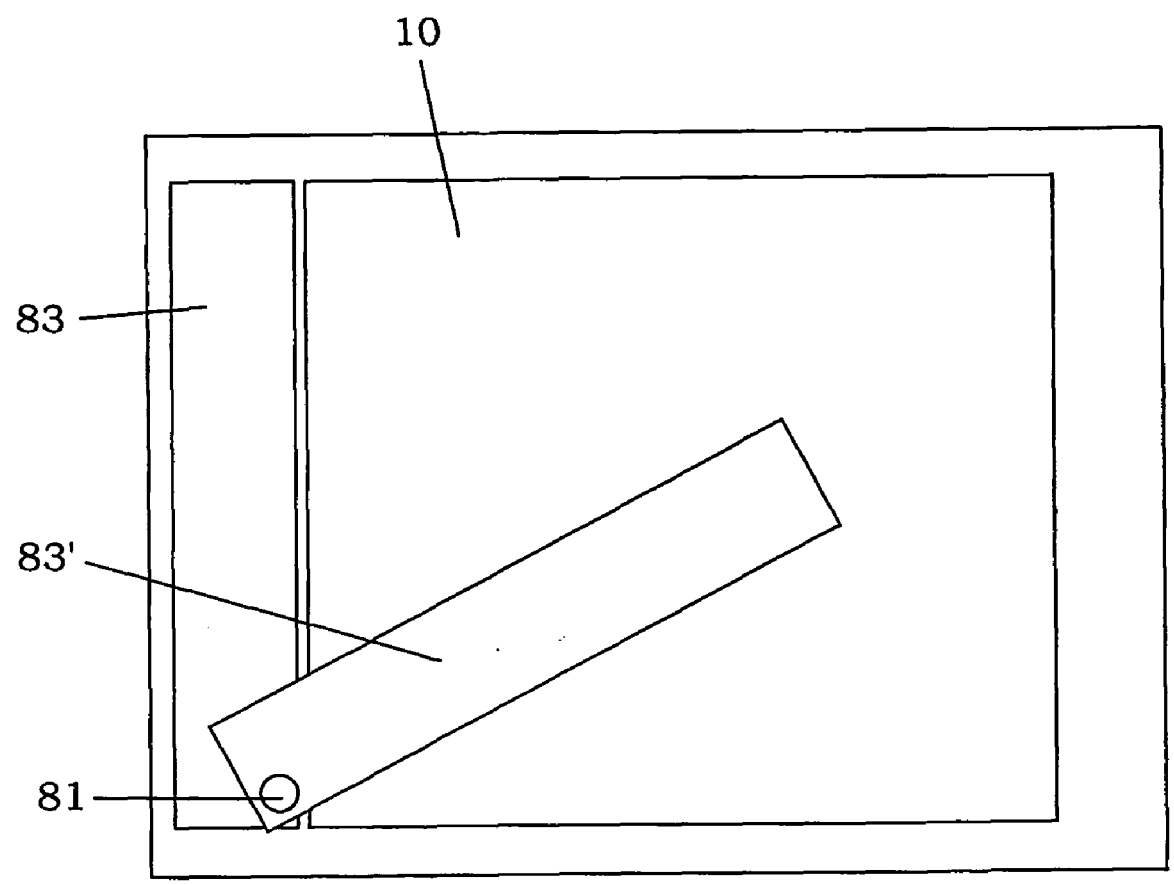
FIG. 8 shows a phantom which is arranged so as to be pivotable at the edge of an X-ray detector.

FIG. 8 shows a further embodiment of an automatically movable phantom. This figure is a plan view of the sensitive surface 10 of an X-ray detector. The strip-like phantom in the standard position (reference 83) is arranged so as to be pivotable about a point 81 in the vicinity of the sensitive surface 10. If required, it can be automatically rotated about the pivot axis extending perpendicularly to the plane of drawing and hence be introduced into the beam path between the radiation source (not shown) and the sensitive surface 10 (position 83').

The device described with reference to the Figures enables automatic adaptation of parameters such as, for example, gain settings, without endangering the hospital staff, patients or other persons and while requiring at the same time only a minimum amount of human supervision. The automatic X-ray calibration can even be performed during the night in the absence of all personnel, thus reducing the costs of maintenance and ensuring an imaging performance which is stable in the course of time.

The invention also enables a purely image-based detection of various faults of components of the X-ray system such as faulty pixels, rows or columns which occur, for example, due to faulty wiring, transistors or line drivers, faulty AD converter chips, corrosion of the scintillator layer, a defective X-ray tube, etc.

The invention claimed is:

1. A method for automatically testing an X-ray imaging system while generating X-rays, comprising the steps of:
    introducing automatically a phantom into a space between an X-ray source and an X-ray detector during a test;
    acquiring at least one image while the phantom is present in the beam path;
    monitoring a defined safe state in a safety zone around the X-ray system by means of sensors; and
    interrupting the generation of X-rays upon detection that the safe state is abandoned.

2. A method as claimed in claim 1, wherein the safe state involves the closed state of at least one entrance to the safety zone.

3. A method as claimed in claim 1, wherein the safe state is defined by a pattern of sensor signals observed during a definition phase.

4. A method as claimed in claim 1, wherein the monitoring of the safe state commences when
    all doors leading to the room in which the X-ray system is installed are closed except for a last door, and
    an activation signal associated with the last door commences while the last door is still open and ends when the last door is closed.

5. A device for the automatic testing of an imaging X-ray system while generating X-rays, which device comprises:
    a device for automatically positioning at least one phantom in a beam path between an X-ray source and an X-ray detector while the test is being carried out;
    at least one sensor for monitoring a safety zone around the X-ray system; and
    a control unit which is coupled to the sensor and to the X-ray system and is arranged to interrupt the generating of X-rays when the sensor signals indicate that a defined safe state is abandoned.

6. A device as claimed in claim 5, wherein the sensors include:
    door contacts for detecting the closed state of entrances;
    motion detectors which operate on the basis of infrared signals, ultrasound signals and/or video monitoring;
    gas detectors, notably carbon dioxide sensors;
    pressure sensors which may be arranged notably on the floor;
    light barriers;
    acoustic sensors and/or
    the X-ray detector of the X-ray system.

7. A device as claimed in claim 5, wherein the phantom is arranged on a flexible carrier which is transported, via guide rollers, in the zone between the X-ray source and the X-ray detector.

8. A device as claimed in claim 5, wherein the phantom is journaled so as to be pivotable about a pivot axis.

9. An apparatus for automatically testing an X-my imaging system while generating X-rays comprising:
- means for automatically introducing, while a test is being carried out, a phantom into an area of the X-ray imaging system between a source of X-rays and a detector of X-rays;
- means for monitoring a defined safe state in a safety zone around the X-ray imaging system by means of sensors; and
- means for interrupting the generation of X-rays upon detection that the safe state is abandoned.

10. The apparatus of claim 9, wherein the means for automatically introducing a phantom comprises guide rollers.

11. A system for calibrating a radiation detecting apparatus, comprising:
- an activation system for enabling an operation of a calibration procedure;
- a phantom that is configured to be automatically positioned in an area between a radiation source and a radiation detector during the calibration procedure;
- at least one sensor for monitoring integrity of a predefined safety area around the radiation detection apparatus to be calibrated; and
- a control system operatively coupled to the at least one sensor and configured to interrupt the calibration procedure based upon a breach of the integrity of the predefined safety area.

12. The system of claim 11, further comprising a plurality of sensors for monitoring the integrity of the predefined safety area around the radiation detection apparatus to be calibrated.

13. The system of claim 12, wherein at least one of the plurality of sensors is selected from the group consisting of an ultrasound motion detector, an infrared motion detector, a video camera, a gas detector, a pressure sensor, a light barrier, an acoustic sensor and a radiation detector.

* * * * *